United States Patent [19]

Smith

[11] Patent Number: 4,668,808

[45] Date of Patent: May 26, 1987

[54] POLYCHROMIUM COMPOUNDS AND PROCESSES TO MAKE SAME

[75] Inventor: Paul D. Smith, Bartlesville, Okla.

[73] Assignee: Phillips Petroleum Company, Bartlesville, Okla.

[21] Appl. No.: 640,059

[22] Filed: Aug. 13, 1984

[51] Int. Cl.$^4$ ............................................. C07F 11/00
[52] U.S. Cl. ........................................ 556/12; 556/28; 556/58; 585/457; 502/152; 502/154
[58] Field of Search ................. 260/438.5; 556/12, 28, 556/58

[56] References Cited

U.S. PATENT DOCUMENTS

| | | | |
|---|---|---|---|
| 3,704,259 | 11/1972 | Bower | 260/438.5 R |
| 3,763,197 | 10/1973 | Collier et al. | 260/438.5 R X |
| 3,969,386 | 7/1976 | Ballard et al. | 260/429 R |
| 4,042,610 | 8/1977 | Manzer | 260/438.5 R X |
| 4,057,565 | 11/1977 | Manzer | 260/438.5 X |

*Primary Examiner*—Helen M. S. Sneed
*Attorney, Agent, or Firm*—A. L. Robbins

[57] ABSTRACT

Polychromium compounds such as octakis($\mu$-trimethylsilylmethyl) tetrachromium(II) as well as a process to make these new compounds are disclosed. The compounds are useful in the production of, e.g., dual valence chromium catalysts useful in the production of linear low density polyethylene.

11 Claims, 2 Drawing Figures

POLYCHROMIUM COMPOUNDS AND PROCESSES TO MAKE SAME

The present invention relates to novel chromium compounds. In another aspect this invention relates to a process to produce polychromium compounds.

BACKGROUND OF THE INVENTION

Many chromium compounds have been described in the literature.

Mono-and-binuclear chromium complexes are known in the art. E.g., tetrakis(trimethylsilylmethyl)-chromium(IV), Cr(TMS)$_4$; bis($\mu$-trimethylsilylmethyl)-bis-[(trimethylphosphone)(trimethylsilylmethyl)]dichromium(II), [Cr$_2$(CH$_2$SiMe$_3$)$_4$(PMe$_3$)$_2$]; bis($\mu$-allyl)-bis(allyl)dichromium(II), Cr$_2$(C$_3$H$_5$)$_4$ having been disclosed by their chemical name. The term "TMS" refers to the trimethylsilylmethyl ligand.

Chromium compounds have a wide variety of utilities depending upon their structure and their specific activities. Certain inorganic hexavalent chromium compounds, in particular, CrO$_3$, have been found to be highly active catalyst components in the catalytic polymerization of ethylene and other olefins. This fundamental discovery has led to significant research and further chromium compounds have been discovered which are useful in the general area of olefin polymerization. It is a continued goal to find new chromium compounds having specific properties rendering them useful for particular applications.

THE INVENTION

It is one object of this invention to provide novel chromium compounds.

Another object of this invention is to provide novel chromium compounds having more than 2 chromium atoms per molecule.

A yet further object of this invention is to provide a process to produce polychromium compounds.

These and other objects, advantages, details, features and embodiments of this invention will become apparent to those skilled in the art from the following detailed description of the invention, the appended claims and the drawings.

In accordance with this invention it has been found that certain novel chromium compounds as defined in the following exhibit unusual and advantageous properties; they are particularly useful as catalyst components or catalyst precursors in catalytic ethylene polymerization.

THE CHROMIUM COMPOUNDS

In accordance with a first embodiment of this invention a group of novel chromium compounds is provided. This group of compounds can be characterized by the following general formula:

$$Cr_n(R)_{2n}$$

wherein n is an integer of 3 or more, preferably 4–6, most preferably n is 4;

R is a ligand having the formula $$-CH_2-MR^1R^2R^3$$

wherein

M is C, Si, Ge, Sn or Pb, preferably Si;

R$^1$, R$^2$, R$^3$, which can be the same or different, are hydrocarbyl substituents consisting of carbon and hydrogen atoms, preferably having 1 to 12 carbon atoms, and usually being selected from the group consisting of alkyl, aryl, alkaryl, aralkyl, alkenyl radicals, alkyl radicals of 1–3 carbons, particularly methyl, being preferred.

Specific examples of compounds of this invention are:

Cr$_4$[CH$_2$C(CH$_3$)$_3$]$_8$

Cr$_4$[CH$_2$Si(CH$_3$)$_2$CH$_2$CH=CH$_2$]$_8$

Cr$_4$[CH$_2$Si(CH$_3$)$_3$]$_8$

Cr$_4$[CH$_2$Si(CH$_3$)$_2$CH$_2$C$_6$H$_5$]$_8$,

Cr$_4$[CH$_2$Si(C$_6$H$_5$)$_3$]$_8$ where C$_6$H$_5$ is phenyl.

The n chromium atoms of the novel compounds of this invention are connected to each other in a single or double ring structure, preferably as one ring of 4 chromium atoms. The ring structure and the above formula are believed to accurately describe the novel compounds. It should be emphasized, however, that complex chemical bonds are involved in the novel molecules of this invention and the details, scientific analysis and description of these compounds are given with the understanding that the invention here involved should not be limited thereby.

Figure 1:
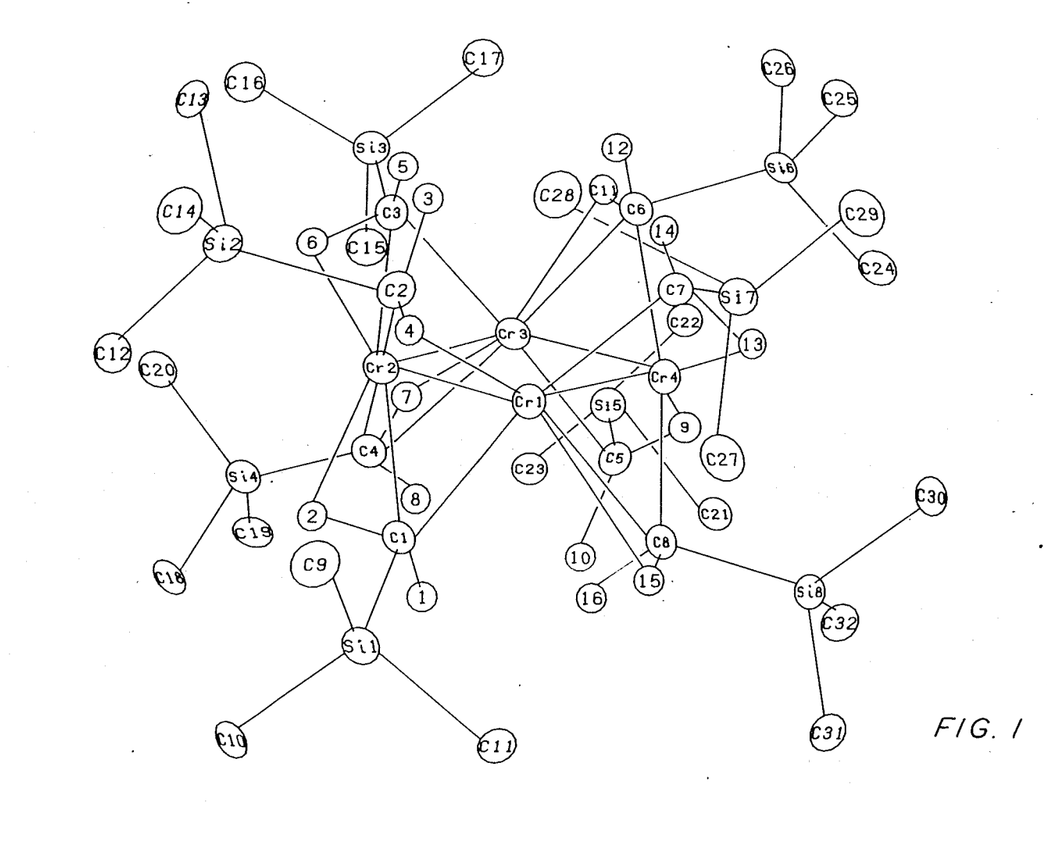
FIG. 1 is a computer generated, simplified structural formula of a molecule of this invention as determined by single crystal x-ray crystallography.
Figure 2:
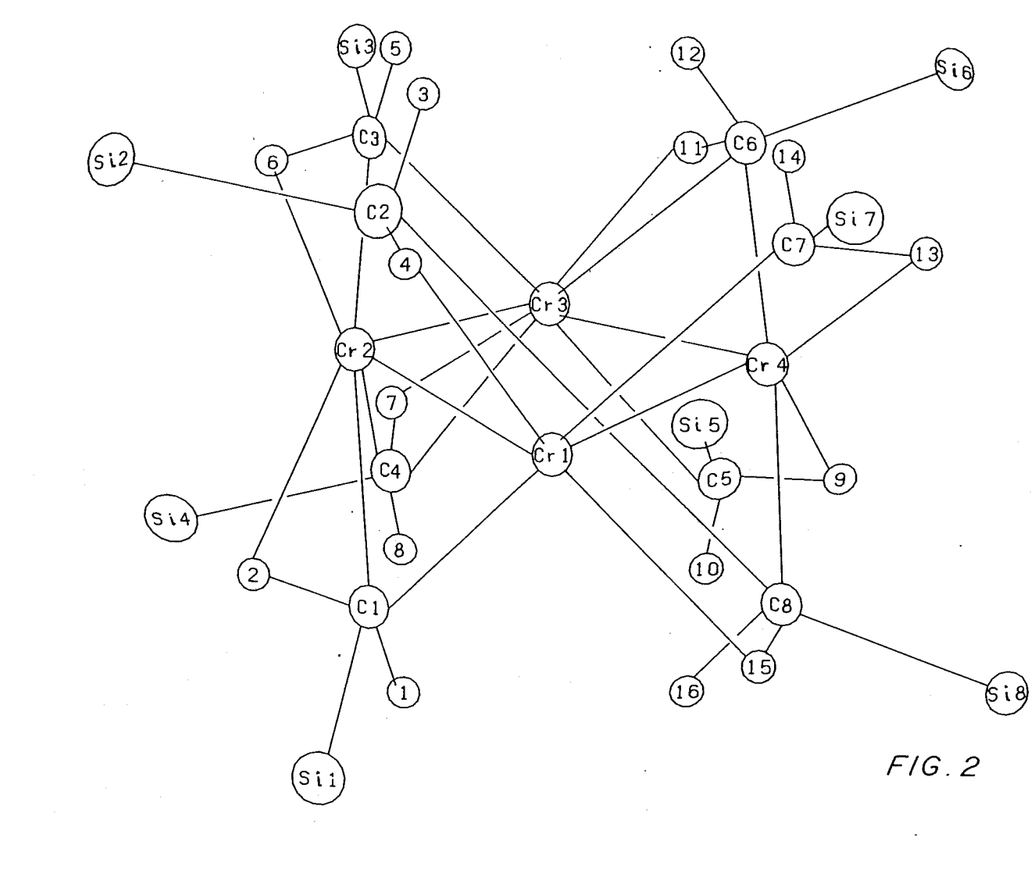
FIG. 2 is a further simplified structural representation of the same molecule shown in FIG. 1.

The presently preferred chromium compound is octakis($\mu$-trimethylsilylmethyl)tetrachromium(II). This compound is schematically shown in FIGS. 1 and 2. In FIG. 1 the hydrogens of the outside methyl groups have been left off for clarity. In FIG. 2 the molecule is shown yet further simplified with all methyl groups left off. Each of the silicon atoms (Si1 to Si8) has 3 methyl groups attached to it.

PROCESS TO PRODUCE POLYCHROMIUM COMPOUNDS

In accordance with a second embodiment of this invention a process to produce polychromium compounds is provided. This process comprises adding a substituting alkylating agent, selected from the group consisting of aluminum, sodium, lithium and magnesium agents having the formula $$Me_xR_yY_z$$

wherein Me is Al, Na, Li, Mg, or Zn.

Y is halogen, preferably chlorine;

R is —CH$_2$—M—R$^1$R$^2$R$^3$ is defined above;

x is 1 or in the case where Me is Al x is 1 or 2;

z is 0 or more;

y+z is the valence or remaining valence of Me$_x$ preferably a magnesium compound having the formula Y—Mg—R, wherein Y is halogen (preferably Cl) or R to a Cr compound CrX$_2$. The preferred process comprises adding a Grignard reagent (Y=halogen) wherein, the substituent R is as defined above to a solution of CrX$_2$ in a solvent and recovering the chromium compound produced thereby from said solvent. X is chlorine, bromine or iodine.

The preferred Grignard reagent used has the general formula XMgR, wherein R and X are as defined above.

The preferred chromium compound used in the process of this invention is $CrCl_2$. Various liquids for suspending the chromium dihalide can be used. It is particularly preferred to use a liquid which increases the solubility of the chromium dihalide in the reaction fluid medium. Thus, a liquid which is a Lewis base is preferred. Ethers can be used. Cyclic ethers such as tetrahydrofuran (THF) are particularly preferred.

The substituting agent, particularly the Grignard reagent, in accordance with this invention is added to the suspension of the chromium halide. It is preferred that the magnesium compound is added in the form of a solution. Ethers are particularly preferred solvents for the magnesium compounds, e.g. the Grignard reagents, here involved. Diethyl ether is the presently preferred solvent for these compounds.

Some of the Grignard reagents here involved are commercially available materials. These products can be conveniently produced by adding a compound having the formula X—R, wherein X is a halide atom and R has the above-defined meaning, chlorine being preferred for X, to finely divided elemental magnesium, such as magnesium turnings, suspended in a dry diluent such as diethyl ether or THF.

In accordance with this invention, it has been found that the order of addition of the reactants is important. It has been found that the Grignard reagent should be added dropwise to a suspension of $CrCl_2$ in the reaction fluid (e.g. THF) to prepare the desired polynuclear chromium complexes. When $CrCl_2$ is added to the Grignard reagent, the prior art Cr complexes are formed. It is presently believed that the same order of addition is to be employed in the case of the other substituting agents as well.

The diluents, solvents and reactants used in the process of this invention are preferably employed in ranges as shown the following table.

TABLE

|  | Broad | Specific |
|---|---|---|
| Substituting agent, preferably YMgR (mole) | 1.8 to 3 | 1.9 to 2.2 |
| Solvent, mL per g agent | 2 to 10 | 3 to 6 |
| $CrX_2$ (mole) | 1 | 1 |
| Diluent, mL per g $CrX_2$ | 50 to 500 | 75 to 150 |

The above tabulation is based on 1 mole of $CrX_2$; fractions or multiples thereof are of course contemplated, as will be apparent to a person skilled in the art.

The compounds of this invention are preferably prepared in a dry, oxygen-free ambient, e.g. under argon, nitrogen or helium at temperatures generally below 0° C., preferably in a temperature range and sufficient pressure to maintain liquid phase conditions, generally at about atmospheric pressure at about −20° C. to about −100° C. The reaction is carried out generally under a pressure maintaining liquid phase, generally at about atmospheric pressure.

The compounds prepared by the reaction step of the process of this invention are recovered by separation techniques including decanting, filtering, washing, drying, particularly vacuum drying. It is presently preferred to extract the product of the reaction step of the inventive process following the solvent removal with hydrocarbon fluids such as alkanes, particularly preferred is n-pentane.

USE OF THE NEW CHROMIUM COMPOUNDS

The novel chromium compounds are useful as catalyst components or precursors for catalysts for olefin polymerization of copolymerization. More specifically, active chromium polymerization catalysts can be produced from the compounds of this invention by contacting an appropriate support with one or more of these compounds. Preferably the support is contacted with a solution of the new compounds.

SUPPORTS

The supports on which the new compounds exhibit their catalytic activity are preferably inorganic oxide containing-supports. Particularly preferred are supports selected from the group consisting of silica, silica-alumina, alumina, fluorided alumina, silated alumina, thoria, aluminum phosphate, phosphated silica, phosphated alumina, silica-titania, coprecipitated silica/titania, and mixtures, thereof, fluorided/silated alumina, being presently preferred, as well as any one or more of these supports containing chromium, preferably chromium in an activated stage such as hexavalent chromium.

One particular application of the new compounds is in olefin polymerization catalysts containing two or more different catalytic sites. Particularly the new compounds of this invention can be employed in dual valence chromium catalyst systems. In these applications, the new chromium compounds are contacted with an already active olefin polymerization catalyst. A preferred dual site catalyst is obtained by contacting one or more of the new chromium compounds with an olefin polymerization catalyst comprising catalytically active chromium sites. An example of such application would be to contact the new chromium compounds with an olefin polymerization catalyst containing hexavalent chromium. In accordance with a preferred use of the new compounds these new chromium compounds are contacted with an activated chromium catalyst, the latter often being referred to as a Phillips catalyst. Such Phillips catalysts are described, e.g.. in U.S. Pat. No. 2,825,721, U.S. Pat. No. 3,887,494, U.S. Pat. No. 4,081,407, U.S. Pat. No. 4,312,967 and U.S. Pat. No. 4,392,967).

The preferred supports used for the production of the catalyst are characterized by the following physical properties:

| | Physical Characteristics of the Preferred Supports | |
|---|---|---|
| Physical Properties | Broad | Specific |
| Pore Volume[1], cc/g | 0.4 to 3.5 | 0.6 to 2.5 |
| Surface Area[2], m²/g | 200 to 800 | 250 to 600 |

[1]As determined by mercury intrusion
[2]As determined by BET (nitrogen absorption)

In order to obtain the catalyst in which the compounds of this invention exhibit the desirable effect in olefin polymerization, these compounds are contacted with the support or with the initial catalyst generally by mixing the support or initial catalyst, a diluent and one or more of the novel compounds. The concentration of the novel compound is not critical and depends to a large extent on the specific use of the catalyst, for instance on the nature of the polymer to be made with such catalyst. As a general rule, however, the novel compounds of this invention are employed in a quantity of 0.1 to 2 parts by weight of chromium per 100 parts by weight of support or initial catalyst.

The new compounds of this invention are applied to the solid support or the initial catalyst preferably in solution form under the usual dry, oxygen-free conditions. Suitable solvents for the compounds in this application are n-pentane, n-octane, cyclohexane, benzene and THF.

The catalysts so obtained with the compounds of this invention are ultimately used to polymerize olefins such as ethylene, propylene, 1-butene, 1-hexene and the like. These polymerization processes are carried out under conditions that are broadly and specifically known in the art. The dual valence chromium catalysts can be used to produce linear low density polyethylene using only ethylene as the feedstock.

The following examples are given to further illustrate preferred features of this invention without undue limitation of its scope.

EXAMPLE I

Comparison, Prior Art Mononuclear Cr Complex

The reactants, $CrCl_2$, Mg and trimethylsilylmethyl chloride (chloromethyltrimethylsilane) (TMSC) were obtained commercially. Reaction solvents were reagent grade, dried over an appropriate drying agent (usually calcium hydride), distilled and stored under argon prior to use. Unless indicated otherwise, all manipulations were carried out in an inert atmosphere of either argon or nitrogen.

2.0 g (80 mmole) of Mg turnings were suspended in 100 mL of THF and brought to reflux. 11 mL (80 mmoles) of TMSC (neat) was added dropwise resulting in a vigorous reaction. After completing the addition the clear solution was stirred one hour and cooled to −30° C. Then 5.0 g (40 mmole) of $CrCl_2$ were slowly added while maintaining a temperature of about −30° C. The reaction solution was then allowed to slowly warm to room temperature (23° C.) resulting in a darkening in color which after about one hour turned blackish-blue. After stirring at room temperature for about 24 hours the solution became royal purple in color. The solvent was removed under vacuum and the residue was extracted with portions of n-pentane until the pentane phase was nearly colorless. The combined extracts were filtered over two grams of activated silica. The filtrate was evaporated to dryness at −78° C. (the product is very soluble in n-pentane and hard to crystallize) resulting in 4.6 g (29% of theoretical) of purple crystals, $Cr(TMS)_4$.

Elemental analysis for $Cr(TMS)_4$, $C_{16}H_{44}Si_4Cr$, molecular weight of 400.4.

|  | C | H |
|---|---|---|
| calculated | 47.94% | 11.06% |
| found | 47.10% | 10.99% |

Mass spectroscopy of the extremely volatile purple crystals showed the molecular ion at 400 mass units. Electronic absorption spectra were identical to published results.

The purple crystals consequently are $Cr(TMS)_4$.

EXAMPLE II

Invention, $Cr_4(TMS)_8$

The reactants, $CrCl_2$ and Grignard reagent (trimethylsilylmethylmagnesium)chloride, were obtained commercially. Reaction solvents were reagent grade, dried and distilled as before. Manipulations were carried out as before.

25 g (203 mmole) of $CrCl_2$ were suspended in 500 mL of THF at −30° C. Then 250 mL of trimethylsilylmethylmagnesium chloride solution (1.6M in diethylether, 400 mmole) were added dropwise over a two hour period while maintaining a reaction temperature of −30° C. The reaction solution was then allowed to slowly warm to room temperature (23° C.). The solvent was removed under vacuum and the remaining residue was extracted with five 300 mL portions of n-pentane. The combined extracts were filtered over 5 g of activated silica. The filtrate was reduced to about 300 mL by vacuum distillation and stored at −78° C. overnight. The resulting brownish-black crystalline mass was recovered by decanting the mother liquor, washing the mass with 500 mL of cold (−78° C.) n-pentane and drying it under vacuum, first at −78° C., then gradually warming to room temperature. The yield was 35.0 g (155 mmole, 76% of theoretical) of a dark brown crystalline product analyzed as follows:

|  | C | H | Cr | Si |
|---|---|---|---|---|
| Calculated | 42.44% | 9.79% | 22.96% | 24.81% |
| Found | 42.28 | 9.89% | 25.34% | 22.49% |

C and H were determined by elemental analysis.
Cr was determined by plasma emission analysis. Analysis is subject to greater experimental error in preparing samples than for the C, H Analyses.
Si was determined by difference.

For the purpose of x-ray diffraction analysis, suitable crystal specimens were mounted under $N_2$ in 0.3 mm Lindemann capillaries.

A. Crystal data: $C_{32}H_{88}Cr_4Si_8$, formula weight=905.73, monoclinic space group of P2-1/n, a=17.067(6)Å, b=13.418(4)Å, c=22.827(8)Å. (Note: The value in parentheses here and later are estimated standard deviations). $\beta=99.85(3)$Å, V=5153.2Å, Z=4, $\rho=1.17$ g/cm, $\mu=10.5$ cm$^{-1}$, Mo-K$\alpha$ radiation ($\lambda=0.71073$Å), temperature $=-100°\pm1°$ C., F(000)=1952, and peak width at half-height=0.30°.

B. Intensity measurements: Three-dimensional X-ray diffraction data were collected from a single crystal (0.20×0.30×0.35 mm) mounted on a computer-controlled Enraf-Nonius CAD4 diffractometer using Mo-K$\alpha$ radiation (graphite monochromator), $\omega$-$\theta$ scan type, a scan rate of 2°-20°/min (in omega), scan width, degrees, of 0.7+0.350 tan $\theta$, maximum 20 of 50.0°. A total of 10,057 total reflections were measured of which 9,122 were unique annd which 5,635 were used in the final refinement. Corrections were Lorentz-polarization, linear decay (from 1.00 to 1.10 on I).

C. Structure solution and refinement: The computer hardware/software employed was a PDP-11/60 based Texray system utilized by Molecular Structures Corporation.

The positions of the Cr and Si atoms were obtained from the best E map computed with the automatic direct-methods routine in the refinement program. Refinement was determined by means of the full-matrix least-squares method. The hydrogen atoms were located from a difference map and included in the refinement with anisotropic temperature factors. The position of 16 hydrogen atoms in the structure were obtained from isotropically refined data. The remaining 72 methyl group hydrogens were included in calculated positions assuming idealized geometries with C—H=0.95Å and were not refined.

The molecular structure of $Cr_4(TMS)_8$ as drawn by the computer is shown in FIG. 1 with the atom-numbering scheme used and the methyl hydrogen atoms omitted for clarity. The main features are the four chromium atoms in an almost square planar configuration linked together by Cr—Cr multiple bonds and through carbon atoms to eight bridging TMS ligands. Each metal-metal bond is bridged by two TMS ligands, one below and one above the plane of the Cr atoms as is perhaps more clearly seen in FIG. 2.

Another feature of the novel compound is the bonding interactions between hydrogen atoms in the bridging positions and the chromium atoms. Each chromium atom has two such bonding interactions represented in FIG. 2, for example, by the units H4—Cr1—H15, H2—Cr2—H6, H7—Cr3—H11 and H9—Cr4—H13.

Analytical results thus confirm the novel compound to be $Cr_4(TMS)_8$.

Catalyst Preparation

Catalysts produced with $Cr_4(TMS)_8$ can be formed in situ in the reactor by injection of separately charged portions of a solution of the organochromium compound and a particulate support as shown in Example III. For example, the desired quantity of a 0.1 molar solution of $Cr_4(TMS)_8$ in n-pentane is flushed into the reactor with a portion of a diluent to be used in the polymerization process, e.g., isobutane, already containing the previously charged support and remaining diluent. Ethylene is then immediately admitted and polymerization commences. No delay for catalyst reaction time is necessary.

The in situ method is also applicable to the formation of multivalent chromium catalysts as shown in Example VI. For example, an activated, supported hexavalent chromium-containing catalyst is charged to the reactor where it reacts with the separately injected organochromium compound to produce the novel catalyst composition.

Catalysts produced with $Cr_4(TMS)_8$ can also be formed by precontact of the organochromium compound and the support in the absence of moisture and oxygen as shown in Example IV. Similarly, a multivalent chromium catalyst can be formed by precontacting the organochromium compound and, for example, a supported activated hexavalent chromium-containing catalyst in the absence of moisture and oxygen as shown in Example VII. The precontact method of catalyst formation may provide a more efficient use of $Cr_4(TMS)_8$ with the support. In this method, for example, a 0.1 molar solution of $Cr_4(TMS)_8$ in n-heptane is contacted with about 1 g of the second component suspended in about 20 to 30 mL of n-heptane. After several minutes of stirring, all the organochromium compound reacts with the second component yielding a light to dark brown colored catalyst and a clear supernatant. The supernatant can be decanted and the catalyst slurry can be used as is or further washed with dry hydrocarbon and subsequently charged to the reactor in slurry form. Alternately, the solvent can be evaporated from the catalyst by gentle heating in a nitrogen or organic atmosphere. The resulting free flowing powder can be charged in that form to the reactor.

EXAMPLE III

The flowing supports were employed: (1) $SiO_2$; Davison Chemical Co. Grade 952 silica, surface area (SA) of about 300 $m^2/g$ and pore volume (PV) of about 1.65 cc/g, activated in a fluidized bed with dry air at 800° C. for 3 hours. (2) $Al_2O_3$; alumina, Ketjen Grade B, SA of about 300 $m_2/g$ and PV of about 1.7 cc/g, activated as above at 600° C. (3) F—$Al_2O_3$; Davison Chemical Co. high pore volume alumina, SA of about 540 $m^2/g$ and PV of about 2.0 cc/g admixed with $NH_4HF_2$ sufficient to provide a calculated 1.8 weight percent fluoride loading, the composite activated as above at 600° C. (4) F—Si—$A_2O_3$; Davison Chemical Co. high pore volume alumina admixed with $NH_4HF_2$ and ethyl silicate 40 (partially hydrolyzed tetraethoxysilane having an equivalent 40 weight percent silica content) sufficient to provide 1.8 weight percent fluoride and a calculated 6 weight percent silica, the composite activated as above at 600° C. (5) $AlPO_4$; aluminum phosphate (P/Al atom ratio of 0.8), SA of about 350 $m^2/g$ and PV of about 1 cc/g, the composite activated as above at 400° C. or 600° C.

Ethylene Polymerization

All polymerization runs were conducted in a 2 liter autoclave reactor under particle form (slurry) conditions containing about 600 g isobutane as diluent and a weighed amount of support as indicated. Generally, the amount of support employed ranged from about 0.02 to about 0.1 g. The temperature employed ranged from 85° to 105° C. (185°–221° F.). The total reactor pressure was held constant in each run at about 565 psi (3.89 Mpa) with ethylene or a combination of ethylene plus hydrogen, when used. The ethylene was supplied on demand from a pressurized reservoir as needed. A run time of 1 hour was normally employed.

Recovered polymers were stabilized with a conventional antioxidant system before physical properties were determined.

The results are given in Table I.

TABLE I

Ethylene Polymerization
Separate Addition of Catalytic Components to Reactor

| Run No. | Support Type | Activated Temp. °C. | $H_2$ psi | $Cr_4(TMS)_8$ mmole g support | Calc. Prod. g/g/hr[a] | MI g/10 min | HLMI g/10 min | Density g/cc |
|---|---|---|---|---|---|---|---|---|
| 1 | $SiO_2$ | 400 | 0 | 0.05 | 400 | 0.07 | 10 | [b] |
| 2 | $SiO_2$ | 800 | 0 | 0.05 | 300 | 0.19 | 32 | 0.9441 |
| 3 | $AlPO_4$ | 400 | 0 | 0.05 | 1000 | 0 | 7.3 | 0.9532 |
| 4 | $AlPO_4$ | 600 | 10 | 0.05 | 600 | 39 | large | 0.9405 |
| 5 | $AlPO_4$ | 600 | 0 | 0.15 | 2200 | 0.01 | 133 | 0.9357 |
| 6 | $Al_2O_3$ | 600 | 0 | 0.15 | 1500 | 0 | 0.03 | 0.9482 |

TABLE I-continued

Ethylene Polymerization
Separate Addition of Catalytic Components to Reactor

| Run No. | Support Type | Activated Temp. °C. | $H_2$ psi | $Cr_4(TMS)_8$ mmole g support | Calc. Prod. g/g/hr[a] | MI g/10 min | HLMI g/10 min | Density g/cc |
|---|---|---|---|---|---|---|---|---|
| 7 | $Al_2O_3$ | 600 | 10 | 0.05 | 1100 | 0.01 | 1.8 | 0.9550 |
| 8 | F—$Al_2O_3$ | 400 | 0 | 0.05 | 200 | — | — | — |
| 9 | F—$Al_2O_3$ | 500 | 0 | 0.05 | 1300 | 0 | 0.01 | — |
| 10 | F—$Al_2O_3$ | 600 | 0 | 0.10 | 4300 | 0 | 0.10 | 0.9484 |
| 11[c] | F—$Al_2O_3$ | 600 | 0 | 0.10 | 3800 | 0 | 0 | 0.9484 |
| 12[d] | F—$Al_2O_3$ | 600 | 0 | 0.10 | 5600 | 0 | 0.34 | 0.9488 |
| 13 | F—Si—$Al_2O_3$ | 600 | 0 | 0.05 | 8900 | 0 | 0.84 | 0.9504 |
| 14 | F—Si—$Al_2O_3$ | 600 | 10 | 0.05 | 3800 | 1.4 | 88. | 0.9591 |

Notes:
[a]Grams polymer per g catalyst
[b]Not determined
[c]Run at 85° C.
[d]Run at 103° C.
[e]Reactor temperature of 96° C., unless indicated otherwise.

The results in Table I demonstrate that active ethylene polymerization catalyst systems result from the interaction in the reactor of the separately added $Cr_4(TMS)_8$ and support. The organochromium compound is most active in the presence of fluorided-alumina (Runs 10-12) and fluorided-silated alumina (Runs 13,14) with calculated productivities ranging from about 3800 to 9000 g/g catalyst/hr. The results indicate a significant improvement over pure alumina (Runs 6,7), aluminum phosphate (runs 3-5) and pure silica (Runs 1,2) in terms of productivity. The activation temperature of the support can have a marked effect on the activity of the catalyst system. For the active fluorided-alumina support, for example, an activation temperature of about 600° C. appears to be about optimum. Activities drop off sharply when activation temperatures of 400° or 500° C. are used (Runs 8,9). Increasing the reactor temperature at which the polymerization is run with a given catalyst system tends to increase catalyst activity. Runs 10, 11 and 12 indicate that raising the reactor temperature from 85° C. to 96° C. to 103° C. increases productivity from 3800 to 4300 to 5600 g/g catalyst/hr. These runs (10-12) also indicate that melt index or high load melt index does not change appreciably with reactor temperature suggesting that temperature alone is not effective in controlling polymer molecular weight with these catalyst systems.

In the presence of hydrogen, each catalyst system (excluding silica, not tested), as expected, produced lower molecular weight polymer relative to that made in the absence of hydrogen. The alumina-based systems were much less responsive to the effects of hydrogen based on the MI and/or HLMI results (MI increased from 0 to 1.4, HLMI increased from 0 to 88, Runs 6-14) than the $AlPO_4$-based system, Runs 3-5 wherein MI increased from 0 to 39, HLMI increased from 7.3 to a large undetermined value.

The polymer densities of about 0.950 g/cc obtained in the absence of hydrogen for the alumina-based systems taken in conjunction with the relatively high molecular weight polymers made as evidenced by the fractional HLMI values suggest that ethylene homopolymers were primarily made.

With the silica-based system, however, the polymer density of about 0.944 g/cc obtained in Run 2 at a MI of about 0.2 are indicative of possible branching in the polymer structure. This catalyst system is not sufficiently active to be commercially attractive.

EXAMPLE IV

Ethylene was polymerized with catalysts formed by contacting the F—Si—$Al_2O_3$ support with the specified organochromium compounds, isolating the solid compositions and using portions of each as before. The results are given in Table II.

TABLE II

Ethylene Polymerization at 95° C.
Precontacted Organochromium/F—Si—$Al_2O_3$ Catalysts

| Run No. | Organochromium, mmole[a] $Cr(TMS)_4$[b] | $Cr_4(TMS)_8$ | $H_2$ psi | Calc. Prod. g/g/hr | HLMI g/10 min | Density g/cc | Flex. Mod., MPa |
|---|---|---|---|---|---|---|---|
| 15 | 0.19 | 0 | 0 | 14,600 | 0.36 | 0.9510 | 1598 |
| 16 | 0.19 | 0 | 5 | 8800 | 14. | 0.9573 | 1078 |
| 17 | 0.19 | 0 | 50 | 2800 | 580. | 0.9629 | 1158 |
| 18 | 0 | 0.19 | 0 | 6200 | 0.39 | 0.9538 | 1180 |
| 19 | 0 | 0.19 | 50 | 3300 | 990. | 0.9656 | 1475 |

Notes:
[a]mmoles per gram of support
[b]Tetrakis-(trimethylsilylmethyl)chromium(IV); comparison The data in Table II show the inventive organochromium compound or a related comparison prior art organochromium compound can be prereacted with an alumina-based support to produce catalytically active compositions for ethylene polymerization. In the absence of hydrogen, the comparison catalyst (Run 10) appears to be substantially more active than the inventive catalyst based on the calculated productivity values of 14,600 vs 6200, respectively. Both catalysts produced polymers of about the same molecular weight, HLMI of about 0.36 to 0.39. The significantly lower polymer densities and flexural moduli of the polymers produced with the inventivve catalyst suggest that they contain greater amounts of short chain branching, however.

EXAMPLE V

Selected polymers produced with the preceding catalysts were further evaluated with respect to molecular weight and short chain branching. The results obtained are set forth in Table III.

and flexural moduli decreased and HLMI increased as the amount of injected $C_4(TMS)_8$ increased from zero in Run 20 to 2.52 mmole/g of hexavalent chromium catalyst in Run 23. Although not shown in the Table it was observed that induction period of about 20–55 minutes (Run 20), typically noted with hexavalent Cr catalysts, was reduced to about 5 minutes upon addition of $Cr_4(TMS)_8$. This suggests that the added Cr compound

TABLE III

Molecular Characterization of Selected Polymers

| Support | Run No. | $M_n^{(a)}$ ($\times 10^3$) | $M_w^{(b)}$ ($\times 10^3$) | $M_z^{(b)(c)}$ ($\times 10^3$) | HI | Me | Et | Bu+ | Total | Et/Bu+ |
|---|---|---|---|---|---|---|---|---|---|---|
| SiO$_2$ | 2 | 19.1 | 274 | — | 14.3 | 0.26 | 0.40 | 0.29 | 0.95 | 1.4 |
| AlPO$_4$ | 5 | 14.7 | 160 | 2740 | 10.9 | 0.14 | 0.11 | 0.12 | 0.37 | 0.92 |
| F—Si—Al$_2$O$_3^{(e)}$ | 15 | 6.2 | 91 | 2020 | 14.7 | 0.10 | 0.19 | 0.19 | 0.48 | 1.0 |
| F—Si—Al$_2$O$_3^{(f)}$ | 19 | 9.5 | 209 | 2500 | 22.0 | 0.09 | 0.19 | 0.19 | 0.47 | 1.0 |

Notes:
$^{(a)}$Determined by C-13 NMR end group analysis.
$^{(b)}$Determined by size exclusion chromatography.
$^{(c)}$z-average molecular weight is the high molecular weight component.
$^{(d)}$Me is methyl, Et is ethyl, Bu+ is butyl to hexyl.
$^{(e)}$Cr compound was Cr(TMS)$_4$.
$^{(f)}$Cr compound was Cr$_4$(TSM)$_8$.

The results given in Table III demonstrate that the catalysts employed in ethylene polymerization produced polyethylenes of varying molecular weights and molecular weight distributions which contain significant amounts of short chain branches, particularly the silica-based catalyst. Gas chromatography has detected olefins of even carbon number in the liquid phase of the polymerization reactions with the catalysts. This suggests that there are several sites on the catalysts. One produces long chain polymers and another produces $C_{2n}$ olefins where n is an integer $\geq 2$. The incorporation of these olefins in the growing polymer chain could account for the observed ethyl and butyl+ branches. However, it does not account for the methyl branching since propylene is absent in the reactor liquid phase. The methyl branching apparently results from some other unknown characteristic of the polymerization mechanism.

EXAMPLE VI

Portions of dual chromium catalyst systems were employed in ethylene polymerization as described before. The results are presented in Tables IV and V.

reduces the supported $Cr^{+6}$ center so that initiation of polymerization is not entirely dependent upon reduction of the center with ethylene alone. The variation in productivity observed ranged from 4100 in Run 20 to 7700 in Run 21 to 1420 in Run 23 also suggests that catalytic activity is increased by addition of the organo-chromium compound but an excess of it can depress activity.

EXAMPLE VII

Ethylene Polymerization

Prereacted Hexavalent Chromium Catalyst and $Cr_4(TMS)_8$

A series of ethylene polymerization runs were carried out as described in Example III wherein the designated activated supported hexavalent chromium catalyst, each containing about 1 weight percent chromium, was contacted with a solution of $Cr_4(TMS)_8$ as before. The 963 cogel catalyst, prior to impregnation with the solution of $Cr_4(TMS)_8$, was activated by heating it for 3 hours at 800° C. in carbon monoxide, cooled to 700° C. in nitrogen, then heated at 700° C. for 3 hours in dry air.

TABLE IV

Ethylene Polymerization
Separate Addition of Hexavalent Cr Catalyst and $Cr_4(TMS)_8$

| Run No. | Cr Cat. No. | $Cr_4(TMS)_8$ mmole/g | Calc. Prod. g/g/hr | MI | HLMI (g/10 min) | Density g/cc | Flex.$^{(a)}$ Mod. MPa | ESCR$^{(b)}$ F$_{50}$, hrs |
|---|---|---|---|---|---|---|---|---|
| 20 | (1) | 0 | 4100 | 0 | 1.67 | 0.9577 | 1428 | — |
| 21 | (1) | 1.92 | 7700 | 0.03 | 3.11 | 0.9464 | 944 | — |
| 22 | (1) | 2.52 | 1420 | 0.05 | 5.11 | 0.9281 | 480 | — |
| 23 | (2) | 0.41 | 5200 | 0.13 | 8.06 | 0.9399 | 706 | >1000 |
| 24 | (2) | 1.32 | 4050 | 0.19 | 8.37 | 0.9372 | 642 | " |
| 25$^{(c)}$ | (2) | 0.23 | 5100 | 0.08 | 6.75 | 0.9520 | 1185 | " |
| 26$^{(c)}$ | (2) | 0.42 | 4450 | 0.22 | 12.0 | 0.9406 | 756 | " |

Notes:
(1) Davison Chemical Company grade 969 MSB catalyst, 1% Cr on microspheroidal silica, activated 3 hours in air at 800° C.
(2) Davison Chemical Company grade 963 cogel catalyst, 1% Cr on silica-titania cogel, activated 3 hours in air at 700° C., for more details see U.S. Pat. No. 4,392,990.
$^{(a)}$Flexural modulus; ASTM D790
$^{(b)}$Environmental stress cracking resistance; ASTM D1693, condition A, F$_{50}$, hours
$^{(c)}$Run with 20 psi hydrogen in reactor Runs 20–22 in Table IV demonstrate at constant reactor conditions in the absence of hydrogen in the presence of the silica-supported catalyst that olymer density It was cooled and stored in nitrogen pending further use. The 969 MSB Cr catalyst component was activated 3 hours in air at 800° C. A portion of each treated catalyst was then tested in ethylene polymerization. The results are set forth in Table V.

total, a Et/Bu+ ratio of about 0.5 and a density of 0.9392 g/cc. However, with the multiple chromium catalysts of this invention, the polymers of invention Runs 21

TABLE V

Ethylene Polymerization
Precontacted Cr$_4$(TMS)$_8$-Supported Cr(+6) Catalyst Compositions

| Run No. | Cr Cat. Support | Cr$_4$(TMS)$_8$ mmole/g Cat. Support | Reactor Temp. °C. | Calc. Prod. g/g/hr | MI (g/10 min) | HLMI | Polymer Density g/cc | Flex. Mod.[a] MPa | ESCR[b] F$_{50}$, hrs |
|---|---|---|---|---|---|---|---|---|---|
| 27 | 963 cogel | 0 | 95 | 3260 | 0.22 | 16 | 0.9634 | 1479 | [c] |
| 28[d] | 963 cogel | 0 | 85 | 3600 | 0.04 | 3.7 | 0.9392 | — | — |
| 29[e] | 969 MSB | 0 | 85 | 4100 | 0 | 1.7 | 0.9577 | 1428 | — |
| 30 | 952 silica[g] | 0.44 | 95 | 270 | 0.19 | 32 | 0.9441 | 678 | — |
| 31 | 963 cogel | 0.03 | 95 | 7500 | 0.21 | 13 | 0.9617 | 1417 | 69 |
| 32 | 963 cogel | 0.06 | 95 | 10800 | 0.37 | 24 | 0.9583 | 1241 | 37 |
| 33 | 963 cogel | 0.19 | 95 | 3930 | 0.60 | 35 | 0.9471 | 912 | 108 |
| 34 | 963 cogel | 0.35 | 85 | 8280 | 0.04 | 6.3 | 0.9388 | 678 | >1000 |
| 35[f] | 963 cogel | 0.35 | 95 | 6600 | 2.4 | 112 | 0.9321 | 603 | 540 |
| 36 | 963 cogel | 0.35 | 100 | 3600 | 1.5 | 112 | 0.9382 | 716 | — |
| 37 | 952 silica[g] | 0.10 | 100 | 4900 | 0.21 | 9.1 | 0.9406 | 872 | >1000 |

Notes:
Runs 27-29 are controls.
[a]ASTM D790
[b]ASTM D1693, condition A
[c]A blank run signifies not determined
[d]Run with 5 ppm triethylborane (TEB), 7 g butene-1, 50 g hexene-1
[e]Run with 5 ppm TEB
[f]Run with 5 psi hydrogen
[g]Davison Chemical Company.

The results in Table V demonstrate in invention Runs 30-37 that active ethylene polymerization catalysts can result from precontacting of inventive catalysts with activated catalysts comprising hexavalent chromium supported on silica and silica-titania. The results in Runs 31-33 show that increasing the Cr$_4$(TSM)$_8$ component from about 0.03 to 0.19 mmole/g catalyst gives a composite catalyst which yields polymers with increasing melt index (about 0.2 to 0.6), decreasing density (about 0.962 to 0.947 g/cc) at constant reactor conditions. The results in Run 34-37 indicate that increasing reactor temperature and/or the addition of hydrogen can significantly increase polymer melt index. Control runs 27-29 show the results obbtained with a prior art supported hexavalent chromium catalyst alone.

EXAMPLE VIII

Selected polymers shown in Tables IV and V were characterized by SEC and NMR methods to ascertain structural features. The results are presented in Table VI.

(density of 0.9399 g/cc), 24 (density of 0.9372 g/cc), 26 (density of 0.9406 g/cc) and 36 (density of 0.9382 g/cc), have total short chain branching ranging from about 1.02-1.60 mole % and Et/Bu+ ratios ranging from about 0.7-1. The differences are significant and demonstrate that it is possible to make medium to low density ethylene polymers (linear low density polyethylene) by employing ethylene as the sole monomer with the catalyst systems of this invention.

EXAMPLE IX

A series of ethylene polymerization runs was made as before at 95° C. using catalysts formed as before by contacting an activated catalyst comprising hexavalent chromium (about 1 weight percent chromium based on the catalyst weight) supported on the silica-titania cogel previously described with the specified organochromium compound. The chromium compounds employed were: (a) dicyclopentadienylchromium, abbreviated Cr(CP)$_2$; (b) dicumenechromium(O), abbreviated Cr(CUM)$_2$ and cited in McDaniel, U.S. Pat. No.

TABLE VI

Molecular Characterization of Selected Polymers (Tables IV,V)

| Run No. | Supported Hex. Cr Cat. | M$_w$ (SEC) ($\times 10^{-3}$) | M$_n$ (NMR) ($\times 10^{-3}$) | HI | Density g/cc | Mole % Branching Me | Et | Bu+ | Total | Et/Bu+ |
|---|---|---|---|---|---|---|---|---|---|---|
| 21 | 969 MSB | 248 | 8.48 | 29 | 0.9399 | 0 | 0.56 | 0.50 | 1.06 | 1.12 |
| 24 | 963 cogel | 281 | 6.79 | 41 | 0.9372 | 0.06 | 0.80 | 0.74 | 1.60 | 1.08 |
| 25 | 963 cogel | 281 | 10.8 | 26 | 0.9520 | 0 | 0.13 | 0.13 | 0.26 | 1.00 |
| 26 | 963 cogel | 239 | 8.37 | 29 | 0.9406 | 0 | 0.58 | 0.53 | 1.11 | 1.09 |
| 28[a] | 963 cogel | 341 | 6.06 | 56 | 0.9392 | 0 | 0.29 | 0.56 | 0.85 | 0.52 |
| 29[b] | 969 MSB | 313 | 7.50 | 42 | 0.9577 | 0 | 0 | 0 | 0 | — |
| 30 | 952 silica | 274 | 1.56 | 175 | 0.9441 | 0.22 | 0.44 | 0.19 | 0.85 | 2.3 |
| 36 | 963 cogel | 103 | 7.86 | 13 | 0.9382 | 0 | 0.64 | 0.86 | 1.50 | 0.74 |
| 37 | 952 silica | 174 | 7.37 | 24 | 0.9340 | 0.05 | 0.87 | 0.75 | 1.67 | 1.16 |

[a]Control ethylene/1-butene/1-hexene terpolymer made only with a hexavalent Cr/silica-titania prior art catalyst
[b]Control ethylene homopolymer made only with a prior art hexavalent Cr/silica catalyst The properties of the polymers shown in Table VI are typical of those made with the indicated catalyst systems. The linear high density polyethylene of Run 29 is shown to be essentially free of short chain branching as expected. The terpolymer of Run 28 shows some short chain branching amounting to about 0.85 mole percent 4,369,295; bis(2,4-dimethylpentadienyl)chromium(II), abbreviated Cr(DMPD)$_2$; and Cr(TMS)$_4$ and Cr$_4$(TMS)$_8$, both described in this application. The results are given in Table VII.

TABLE VII

Ethylene Polymerization Precontacted Hexavalent Chromium Catalyst and Organochromium Compound

| Run No. | Organochromium Compound Type | mmole/g catalyst | Calculated Product g/g/hr | HLMI g/10 min. | Density g/cc |
|---|---|---|---|---|---|
| 38 | Cr(CP)$_2$ | 0.20 | 1 | — | — |
| 39 | Cr(CUM)$_2$ | 0.20 | 6400 | 10 | 0.9529 |
| 40 | Cr(DMPD)$_2$ | 0.20 | 10900 | 18 | 0.9616 |
| 41[a] | Cr(TMS)$_4$ | 0.30 | 8800 | 6.1 | 0.9562 |
| 42 | Cr$_4$(TMS)$_8$ | 0.19 | 3900 | 35 | 0.9471 |

[a] Run at 100° C. to increase polymer MI into the range of the others.

The results in Table VII indicate that the type of organochromium compound employed in the precontacting of the activated, supported hexavalent catalyst has a significant effect on catalyst activity as well as on the physical properties of the resulting polymers. Based on equivalents of organochromium added, comparison Run 38 shows that Cr(CP)$_2$ yielded a dead catalyst. The compound Cr$_4$(TMS)$_8$, invention Run 42, was the most effective in lowering polymer density suggesting that significant short chain branching is present as verified in earlier examples. The other organochromium compounds, in order of effectiveness in lowering polymer density are Cr(CUM)$_2$, Cr(TMS)$_4$ and Cr(DMPD)$_2$, in comparison Runs 39, 41, 40, respectively.

EXAMPLE X

A series of ethylene polymerization runs was made as before at 100° C. using catalysts formed by contacting the previously described activated hexavalent chromium/silica-titania catalyst with either Cr(CUM)$_2$ or Cr$_4$(TMS)$_8$ and isolating the catalyst compositions. At the conclusion of each run, the reactor liquid phase was sampled by gas chromatography to determine the presence of ethylene oligomers. The column could not separate butenes from the isobutane diluent employed in the reactor, hence values for 1-butene are missing. Higher olefins are of greater concern, however, due to the greater probability of being retained in recovered polymer fluff in vapor or liquid form and causing odor, smoking and sticky problems in processing. Polymerization time in run 43 was 12 minutes, in run 44 was 11 minutes, in run 45 was 15 minutes and in run 46 was 60 minutes. The results obtained are given in Table VIII.

TABLE VIII

Higher Olefin Content of Reactor Liquid

| Run No. | Organochromium Compound Type | mmole/g catalyst | Polymer Density g/g/hr | 1-Olefins Detected, Wt. % C$_6$= | C$_8$= | C$_{10}$= | C$_{12}$=+ |
|---|---|---|---|---|---|---|---|
| 43 | Cr(CUM)$_2$ | 0.3 | 0.945 | 0.97 | 0.31 | 0.27 | 0.13 |
| 44 | Cr$_4$(TMS)$_8$ | 0.3 | 0.939 | 0.52 | 0.10 | — | — |
| 45 | Cr$_4$(TMS)$_8$ | 0.3 | 0.952 | 0.16 | 0.03 | — | — |
| 46 | Cr$_4$(TMS)$_8$ | 0.3 | 0.958 | 0.04 | 0.01 | — | — |

The results set forth in Table VIII demonstrate that the invention composite catalyst of Runs 44–46 produce only small amounts of C$_6$= and C$_8$= olefins, the absolute quantities of which increase with decreasing polymer density. However, in the production of polymer of about the same density, the control catalyst of Run 43 produced about 6 times the amount of C$_6$= olefins and about 10 times the amount of C$_8$= as did the invention catalyst of Run 45. The control catalyst also produced significant amounts of C$_{10}$=, C$_{12}$= and higher olefins whereas none were detected with invention catalyst.

EXAMPLE XI

Ethylene as the sole monomer was polymerized in a stirred 2 liter reactor in the gas phase with a dual valence chromium catalyst. The catalyst was prepared under the usual dry, oxygen-free conditions by impregnating a previously activated 963 cogel catalyst (see Example VII) containing about 1 weight percent hexavalent chromium with sufficient Cr$_4$(TMS)$_8$ dissolved in n-pentane to provide 0.2 mg atom of added divalent Cr per gram of cogel catalyst. This corresponds to about 1 weight percent added divalent Cr as Cr$_4$(TMS)$_8$ based on the weight of cogel catalyst plus Cr compound. Following impregnation, the solvent was removed by heating the mixture under a nitrogen stream to dryness at about 50°-60° C. The dual valence chromium catalyst was stored under nitrogen.

Polymerization was conducted in the 2 liter stirred reactor by purging it with nitrogen, heating it to near the desired temperature, charging the catalyst and pressuring the reactor to the specified level with ethylene. As before, ethylene was supplied on demand from a pressurized reservoir during each 1 hour run. The reactor temperature was somewhat difficult to control under the conditions employed.

The reactor temperatures, pressures and resulting polymer properties are shown in Table IX.

TABLE IX

Ethylene Polymerization, Gas Phase

| | Run No. 47 | Run No. 48 | Run No. 49 |
|---|---|---|---|
| Reactor Conditions | | | |
| Temperature (°F.) | 190 to 196 | 207 to 237 | 203 to 239 |
| Pressure (psia) | 215 | 315 | 315 |
| Polymer Properties | | | |
| Density (g/cc) | 0.9510 | 0.9480 | 0.9460 |
| MI (g/10 min) | 0.28 | 1.5 | 2.9 |
| HLMI (g/10 min) | 22.6 | 65.3 | 126 |
| Flex. Modulus (MPa) | 1079 | 1049 | 965 |
| Branching Structures | | | |
| Isolated (Ethyl Branches | 0.315 | 0.279 | 0.225 |
| Branches (Butyl Branches | 0.465 | 0.576 | 0.631 |
| (Fraction) (Hexyl and longer | 0.220 | 0.145 | 0.144 |
| Total Isolated Branches (mole %) | 0.40 | 0.71 | 0.92 |
| Clustered Branches (mole %) | 0.02 | 0.05 | 0.08 |
| Total Branching (mole %) | 0.42 | 0.76 | 1.00 |
| Branch Dispersity | | | |
| Observed (%) | 97.2 | 96.2 | 96.0 |
| Random (%) | 99.6 | 99.2 | 99.0 |
| Relative (%) | 97.6 | 97.0 | 97.0 |
| Saturated/Vinyl End Group Ratio | 1.061 | 1.209 | 1.403 |

The microstructure of the polymer has been obtained by NMR methods. The above example shows that the dual valence chromium catalyst described can be utilized not only in slurry polymerization but also in gas phase polymerization to produce polymers from ethylene having, however, a significant amount of short branches of even carbon number.

Reasonable variations and modifications which will become apparent to those skilled in the art can be made in this invention without departing from the spirit and scope thereof.

What is claimed is:

1. Chromium compound having the formula $$Cr_n(R)_{2n}$$

wherein
n is 4;
R is a ligand having the formula $$-CH_2-MR^1R^2R^3$$

wherein
M is C, Si, Ge, Sn or Pb;
$R^1$, $R^2$, $R^3$, which can be the same or different, are hydrocarbyl substituents consisting of carbon and hydrogen atoms.

2. Compound in accordance with claim 1 wherein M is Si.

3. Compound in accordance with claim 1 wherein $R^1$, $R^2$, $R^3$ each are alkyl radicals of 1 to 3 carbon atoms.

4. Compound in accordance with claim 3 wherein the alkyl radicals are methyl.

5. Octakis(μ-trimethylsilylmethyl)tetrachromium(II).

6. Process to produce a polychromium compound having the formula $Cr_n(R)_{2n}$ wherein n is an integer of 3, 4, 5 or 6, and R is $-CH_2-M-R^1R^2R^3$ comprising adding a compound in a solvent, said compound having the formula $Me_xR_yY_z$ wherein
Me is Al, Na, Li, Mg, or Zn;
Y is halogen;
R is as defined above
M is C, Si, Ge, Sn or Pb;
$R^1$, $R^2$, $R^3$, which can be the same or different, are hydrocarbyl substitutents consisting of carbon and hydrogen atoms
x is 1 or in the case where Me is Al, x is 1 or 2;
y is at least 1;
z is 0 or more;
y+z is the valence or remaining valence of $Me_x$; to a suspension of a chromium compound in a liquid, said chromium compound having the formula;

$$CrX_2,$$

wherein X is chlorine, bromide or iodine said $Me_xR_yY_z$ compound being present in an amount within the range of 1.8 to 3 moles per mole of said chromium compound, said process being carried out under dry oxygen-free conditions at a temperature below 0° C. under sufficient pressure to maintain a liquid phase to produce said polychromium compound in said liquid.

7. Process in accordance with claim 6 wherein $CrCl_2$ is used as said chromium compound.

8. Process in accordance with claim 6 wherein tetrahydrofuran is used as said liquid.

9. Process in accordance with claim 6 wherein a solution of a Grignard reagent having the formula $$XMgR$$

is slowly added to a suspension of $CrCl_2$ in tetrahydrofuran, and wherein the polychromium compound is recovered from the reaction mixture, and wherein said solvent is used in an amount within the range of 2 to 10 mL per gram of said Grignard reagent and wherein said tetrahydrofuran is used in an amount within the range of 50 to 500 mL per gram of said chromium compound.

10. Process in accordance with claim 9 wherein R is trimethylsilylmethyl and X is Cl.

11. A process according to claim 9 wherein said polychromium compound is octakis(μ-trimethylsilylmethyl)tetrachromium(II).

* * * * *